(12) United States Patent
Karkanias et al.

(10) Patent No.: US 7,860,793 B2
(45) Date of Patent: Dec. 28, 2010

(54) SMART SECURE STORAGE

(75) Inventors: Chris Demetrios Karkanias, Sammamish, WA (US); Hubert Van Hoof, Seattle, WA (US); Oren Rosenbloom, Redmond, WA (US); James R. Hamilton, Bellevue, WA (US); Pablo Argon, Redmond, WA (US); Vladimir Sadovsky, Redmond, WA (US); Behrooz Chitsaz, Bellevue, WA (US); Sean Patrick Nolan, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 92 days.

(21) Appl. No.: 12/061,000

(22) Filed: Apr. 2, 2008

(65) Prior Publication Data

US 2009/0254466 A1 Oct. 8, 2009

(51) Int. Cl.
*G06Q 40/00* (2006.01)
(52) U.S. Cl. ....................................................... 705/41
(58) Field of Classification Search .................... 705/41
See application file for complete search history.

(56) References Cited

U.S. PATENT DOCUMENTS

| | | | | |
|---|---|---|---|---|
| 4,491,725 | A | * | 1/1985 | Pritchard ........................ 705/2 |
| 5,995,965 | A | * | 11/1999 | Experton ....................... 707/10 |
| 6,031,910 | A | * | 2/2000 | Deindl et al. ................ 380/255 |
| 6,073,106 | A | * | 6/2000 | Rozen et al. .................... 705/2 |
| 6,131,090 | A | * | 10/2000 | Basso et al. ................... 707/10 |
| 6,925,439 | B1 | | 8/2005 | Pitroda |
| 7,426,475 | B1 | * | 9/2008 | Tangellapally et al. ......... 705/3 |
| 2001/0032099 | A1 | * | 10/2001 | Joao ............................... 705/3 |
| 2001/0041991 | A1 | * | 11/2001 | Segal et al. ..................... 705/3 |
| 2002/0188473 | A1 | * | 12/2002 | Jackson ......................... 705/2 |
| 2003/0040940 | A1 | * | 2/2003 | Nehammer ..................... 705/3 |

(Continued)

FOREIGN PATENT DOCUMENTS

EP 1736925 A1 12/2006

OTHER PUBLICATIONS

Roderick Neame. Smart Cards—The Key to Trustworthy Health Information Systems, BMJ 1997;314:573 (Feb. 22), 8 pages. http://www.bmj.com/cgi/content/full/314/7080/573. Last accessed Oct. 25, 2007.

(Continued)

*Primary Examiner*—James Kramer
*Assistant Examiner*—Lindsay M. Maguire
(74) *Attorney, Agent, or Firm*—Lee & Hayes, PLLC (57) ABSTRACT

A healthcare smart card management system stores a large amount of healthcare information to overcome shortcomings of separate and largely paper medical and insurance files. Embedded security technology supports partial or separated identity proofing as well as hardware time limited storage. Dynamic contextual privacy consent enhances user, healthcare provider, and insurer privacy and proprietary information to encourage and enable universal adoption. Data is structured in self-executing ("print to device") for legacy systems as well as in rolled-access format and archival format to balance usage and data integrity purposes. A plurality of network interfaces are incorporated as well as financial transaction codes. Card integrity is enhanced by remote usage oversight, self-destruct monitoring (e.g., time, location, hacking, malfunction, etc.), and integral write-only audit logs. Levering excess storage capacity, a user can store related healthcare information such as exercise regimen, diet journal, emergency contact information, urgent medical conditions for first providers, etc.

16 Claims, 8 Drawing Sheets

U.S. PATENT DOCUMENTS

| | | | |
|---|---|---|---|
| 2003/0121972 | A1 | 7/2003 | Lee et al. |
| 2003/0154411 | A1 | 8/2003 | Hovik |
| 2004/0232219 | A1 | 11/2004 | Fowler |
| 2005/0197859 | A1* | 9/2005 | Wilson et al. .................. 705/2 |
| 2006/0010007 | A1* | 1/2006 | Denman et al. ................ 705/2 |
| 2006/0173712 | A1 | 8/2006 | Joubert |
| 2006/0173718 | A1 | 8/2006 | Murphy |
| 2007/0239487 | A1 | 10/2007 | Abraham-Fuchs et al. |

OTHER PUBLICATIONS

Siemens, Personal Health Card, Helps to Improve Patient Care and Reduce Costs by Enabling Portable and Secure Patient Information, 2 pages. http://enterprise.usa.siemens.com/products/solutions/security/rightColumn Paragraphs/04/document/D1819__00c.pdf. Last accessed Oct. 25, 2007.

E-Health Insider, Patients Can Carry Records on Secure Smartcard, 5 pages http://www.e-health-insider.com/news/item.cfm?ID=2470. Last accessed Oct. 25, 2007.

Michael Kanellos. Under-the Skin ID Chips Move Toward U.S. Hospitals. Published on ZD Net News, Jul. 27, 2004. 12 pages. http://news.zdnet.com/2100-9584__22-5285815.html. Last accessed Nov. 2, 2007.

Smart Card Makes Medical History: News—ZDNET Australia. Jul. 18, 2001. http://www.zdnet.com.au/news/soa/Smart-card-makes-medical-history/0,139023165, 120243364,00.htm. 5 pages.

* cited by examiner

SMART SECURE STORAGE

BACKGROUND

Smart cards having electronic memories have been increasingly distributed for facilitating transactions (e.g., security access, authenticated identification, healthcare information storage, financial transfers, etc.) Generally, in order avoid misuse, a proprietary and centrally controlled system is fielded with a card issuing authority that stores healthcare information on a smart card for a healthcare insurer. Participating healthcare providers are provided the necessary access protocols, passwords, etc. in order to use these cards. The insured user of the healthcare smart card is limited to using the card as proof of insurance. While such conventional healthcare smart cards are successful to a degree in preventing fraud and to simplifying healthcare data transmission to a healthcare provider, such approaches prove wanting in addressing a number of situations.

For example, the user may prefer or be entitled to utilize a healthcare provider who lacks the proprietary infrastructure in order to access or write to a conventional healthcare smart card. However, it would be beneficial to capture information associated with such a visit so that the user's healthcare records are complete. Unfortunately, flexibility in interfacing to healthcare smart cards is apparently not deemed practical. In particular, ownership of such data as well as legal restrictions on allowable access can be complicated.

As another example, with increasing functionality of smart card technology, an opportunity is presented to seamlessly maintain a wider array of healthcare information without the detriments of traditional paper medical files. However, the types of such information that is appropriate for any given party (e.g., insurer, healthcare specialist, general physician, first responder, etc.), is generally not the entire medical file for a user. Apprehensiveness of loss of privacy can thwart acceptance of such smart card technology.

Moreover, reliance upon a healthcare smart card in lieu of a plurality of healthcare paper files or separate databases is complicated by needs for ready access in urgent care situations while preserving data integrity and backup for archival purposes.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The subject innovation relates to systems and/or methods that provide a smart card for healthcare transactions that enhances a user's privacy while facilitating a broad range of legacy and conforming smart card terminals used by healthcare providers.

In accordance with one aspect of the subject innovation, a method is provided for facilitating healthcare information exchange via a smart card. A first party is authenticated for accessing a healthcare smart card. A first data object is stored in a memory of the healthcare smart card having access limited to the first party. A second party is authenticated for accessing the healthcare smart card. A second object is stored in the memory of the healthcare smart card having access limited to the second party.

In another aspect, a method is provided for facilitating healthcare information exchange via a smart card with enforcing privacy by receiving user settings for consent management of a healthcare smart card specifying parsed access to data stored thereon. Parties accessing the healthcare smart card are authenticated. An authenticated party is limited to a portion of the stored data corresponding to the consent management settings. Data objects are selectively recorded in one of a self-executing format, an archive format, and a rolled-access format on the healthcare smart card.

In an additional aspect, a smart card facilitates healthcare information exchange by including a communication interface, a random access memory for storing healthcare data tagged by category, an access authentication component, a user consent management module for parsing access to the stored healthcare data by category and party, an archiving component to preserve selected stored healthcare data, and a self-destruct component responsive to a triggering event.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

A healthcare smart card management system stores a large amount of healthcare information to overcome shortcomings of separate and largely paper medical and insurance files. Embedded security technology supports partial or separated identity proofing as well as hardware time limited storage. Dynamic contextual privacy consent enhances user, healthcare provider, and insurer privacy and proprietary information to encourage and enable universal adoption. Data is structured in self-executing ("print to device") for legacy systems as well as in rolled-access format and archival format to balance usage and data integrity purposes. A plurality of network interfaces is incorporated as well as financial transaction codes. Card integrity is enhanced by remote usage oversight, self-destruct monitoring (e.g., time, location, hacking, malfunction, etc.), and integral write-only audit logs. Levering excess storage capacity, a user can store related healthcare information such as exercise regimen, diet journal, emergency contact information, urgent medical conditions for first providers, etc.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, terms "component," "system," "interface," "store," "device," "network," "cloud," and the like are intended to refer to a computer-related entity, either hardware, software (e.g., in execution), and/or firmware. For example, a component can be a process running on a processor, a processor, an object, an executable, a program, a function, a library, a subroutine, and/or a computer or a combination of software and hardware. By way of illustration, both an application running on a server and the server can be a component. One or more components can reside within a process and a component can be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Specifically, the subject innovation can be utilized with a variety of hardware configurations such as, but not limited to disability assisted input/output facilities, voice enabled input/output, tactile (e.g., Braille, etc.) keyboard, etc. Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Figure 1:
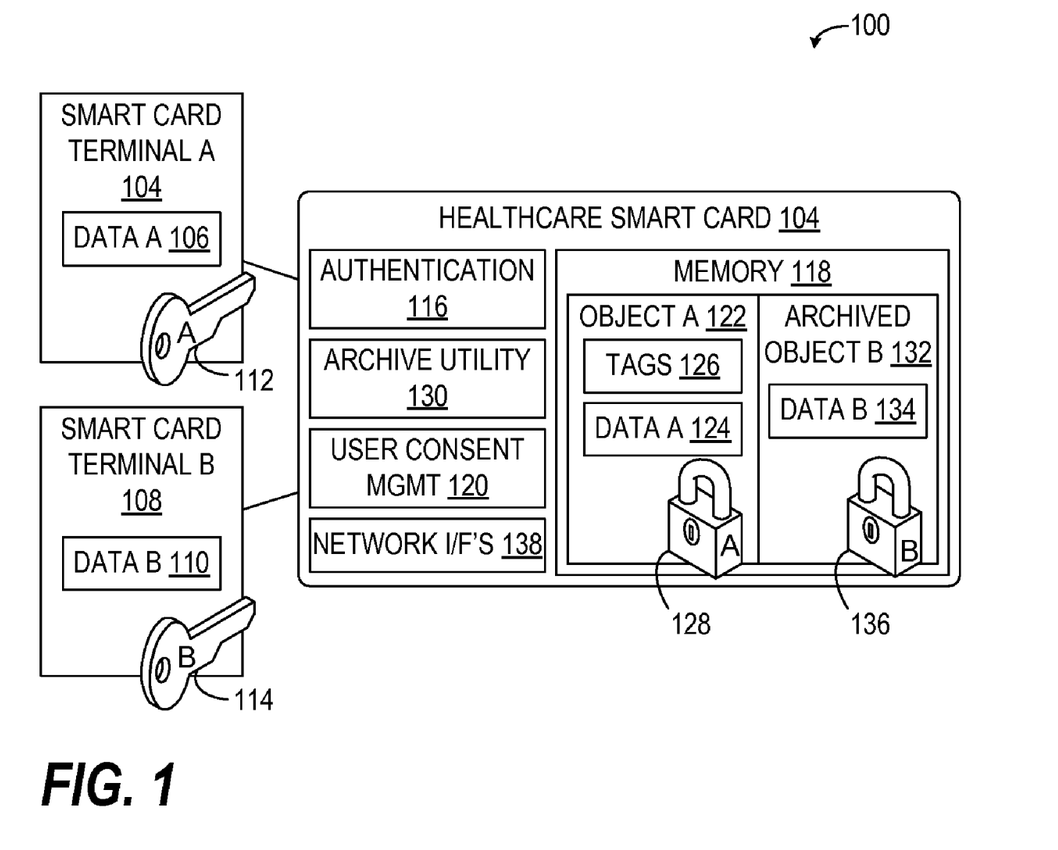
FIG. 1 illustrates a block diagram of an exemplary system that facilitates parsing access to data stored on a healthcare smart card in accordance with consent management settings.

Now turning to the figures, FIG. 1 illustrates a system 100 for facilitating healthcare information exchange using a healthcare smart card 102 between a plurality of parties (e.g., card holder, insurer, oversight entity, archival entity, healthcare providers, legal successor to other parties, etc.), depicted as a smart card terminal A 104 having healthcare data A 106 and a smart card terminal B 108 having healthcare data B 110. Each smart card terminal 104, 106 has a respective authentication/access key 112, 114 for gaining access through an authentication component 116 of the smart code 102. In particular, portions of data in a memory 118 of the smart card 102 can be restricted to particular parties (e.g., A or B) or particular types of parties (e.g., insurer, healthcare provider, healthcare specialist, archivist, etc.).

A user consent management 120 can parse access/control of portions of the memory 118 or particular data objects in memory 118. In the illustrative depiction, a data object A 122 contains data A 124 obtained from smart card terminal 104 with tags 126 that identifying useful information (e.g., original, privileges, expiration data, payment, type of provider, etc.). In order enhance consent managements or discriminated ownership/privacy, a data protection lock A 128 is imposed upon the data A that can be unlocked by the authentication/access key 130 controlled by the smart card terminal A 104.

It should be appreciated with the benefit of the present disclosure that the data object A 122 can be received as a "print to device", utilizing the smart card 102 as a flash memory by a legacy or nonconforming system unable to otherwise interact with functionality of the smart card 102. By so doing, the smart card 102 can carry around data that would otherwise remain held by the originating party. Moreover, the data object A 122 can comprise an executable object that provides user interface functionality to the data A 124 that is generally computer platform and application independent.

An archive utility 130 of the smart card 102 can format a data object, such as an archived data object B 132, depicted as containing data B 134 from smart card terminal 106 and locked as depicted at 136 for accessing with authentication/access key 114. This archival format can enhance data integrity and verification, can increase storage capacity, can prepare data for secure remote archiving, etc.

Advantageously, a plurality of network interfaces 138 on the healthcare smart card 102 can increase the universality and functionality of the healthcare smart card, taking advantage of more types of smart card terminals 104, 108.

Figure 2:
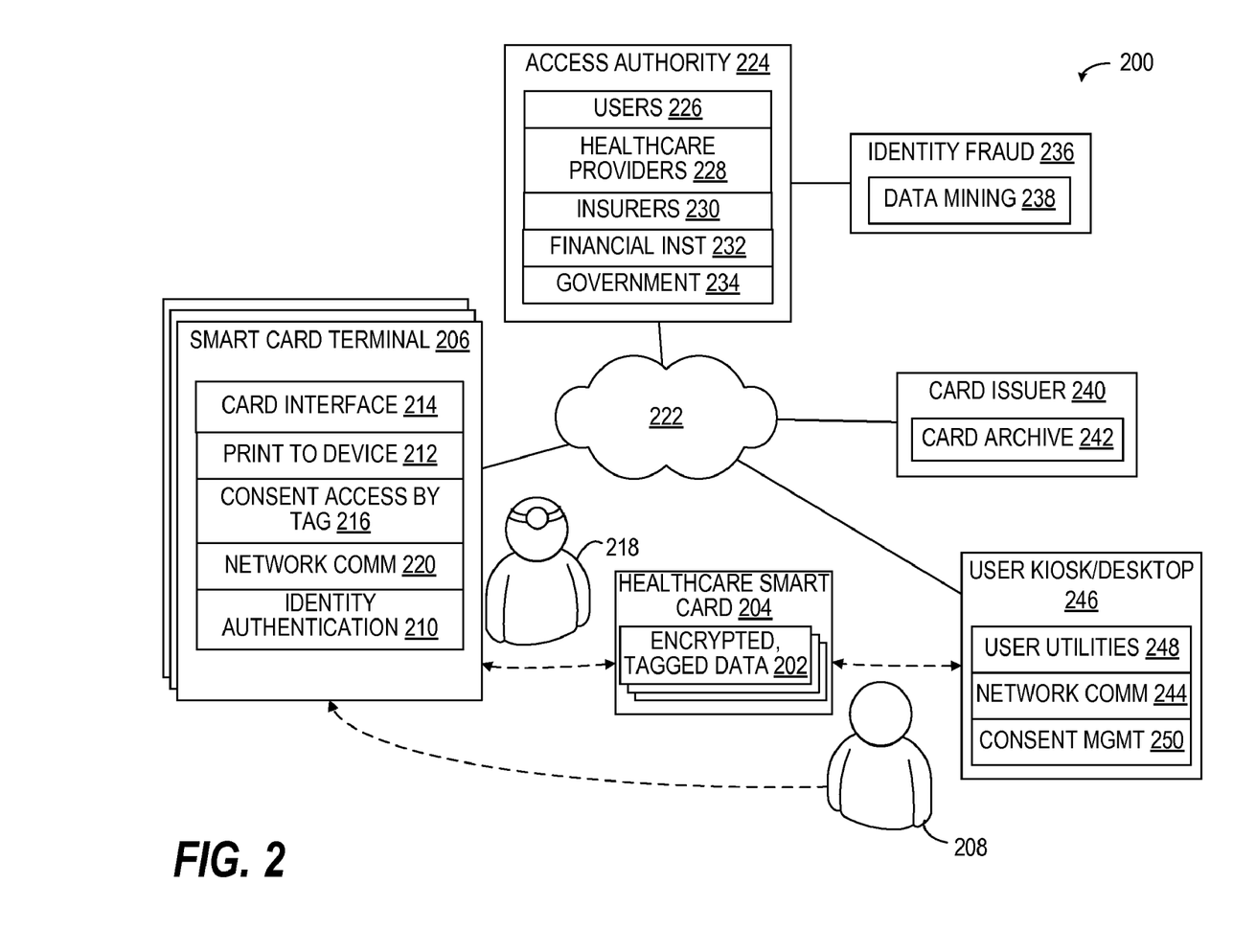
FIG. 2 illustrates a block diagram of an exemplary system for facilitating parsing access of data, archiving of data, and oversight of usage of a healthcare smart card.

In FIG. 2, an exemplary system 200 facilitates healthcare information in the form of a plurality of encrypted and tagged data objects 202 stored securely on a healthcare smart card 204. A smart card terminal 206 can verify that a user 208 has verifying passwords or biometric data (e.g., fingerprint, retina pattern) with an identity authentication component 210. Support for legacy/noncompliant systems is provided by taking advantage of print to device functionality 212 of the smart card terminal 206, which results in printed image being stored onto the smart card 204. For example, a card interface 214 can be a generally available universal serial bus (USB) or other general purpose computer interface. The terminal 206 can query the smart card 204 for applicable data by utilizing a consent access by tag component 216, finding those objects that are permitted or owned by a party using the smart card terminal 206, depicted as a healthcare provider 218. Certain data can be sent via a network communication component 220 to a network (e.g., wide area network, local area network, ad hoc network, Internet, etc.) 222 for purposes such as synchronization, etc.

For instance, an access authority 224 can control access privileges for various parties or their successors, depicted as a user database 226, a healthcare provider database 228, insurer database 230, financial institution database 232, and a government database 234. An illustrative use is depicted as an identity fraud component 236 that performs data mining 238 to detect misuse.

In order to enhance user privacy and data integrity, the healthcare smart can 204 can be periodically backed up, such as by a card issuer 240, in order to obviate risks of card loss of damage. The card archive 242 can receive a portion of the data 202 on the smart card 204, such as excluding data 202 owned by a healthcare provider 218 that does their own backup and restricts distribution beyond the smart card 204 itself. The card archive 242 can include user supplied information entered via a network communication component 244 to a user kiosk/desktop 246 entered with user utilities 248 and a consent management component 250, with an example discussed below regarding FIG. 5.

Figure 3:
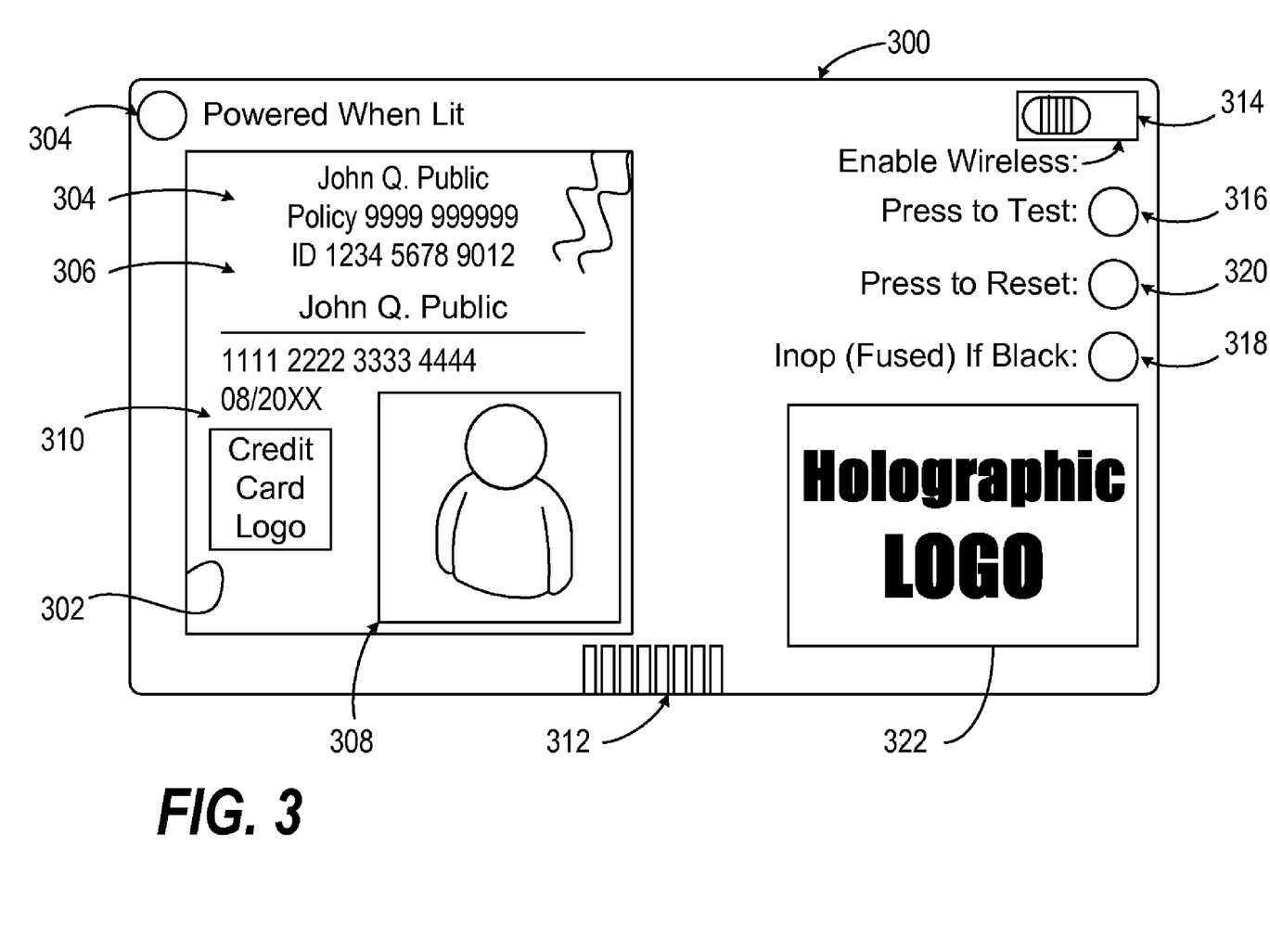
FIG. 3 illustrates a depiction of a healthcare smart card having human perceptible indicia of privacy and functionality.

In FIG. 3, a card holder (user 208 of FIG. 2) can gain enhanced sense of confidence in a smart card 300 by incorporating interactive controls and displays. For example, a low cost thin-film display 302 can generally be off to save power to enhance privacy of the user. Thus, unlike conventional insurance cards and credit cards, identifying information 304, signature depiction 306, photograph 308 and credit card number/logo 310 can be selectively displayed when proper authorization has been provided to the card 300, such as through a contact interface 312.

Rather than being unable to affect the data on the card without a terminal, the smart card 300 can advantageously include other lower power indicator and inputs. For example, a slide button 314 can disable wireless transmission/reception to save battery/ultracapacitor charge. Alternatively or in addition, the disabling button 314 can prevent inadvertent coupling to a near field communication or a wireless communication network (e.g., wide area network, Wi-Fi, PAN, BLUE TOOTH, etc.). Press to test button, depicted as a recessed microswitch 316 can temporarily power indicator lights or the thin film display 302 with functionality/status indicated. Alternatively or in addition, malfunction or self-destruction can cause an indicator depicted at 318 to have a visual state apparent even when the smart card 300 is not powered. A press to reset button 320 can reset a processor (not shown) that is malfunctioning or clear the data. Indicia of being compliant with a privacy protocol ("Holographic Logo") 322 can provide a branding of otherwise not apparent features incorporated into the smart card 300.

Figure 4:
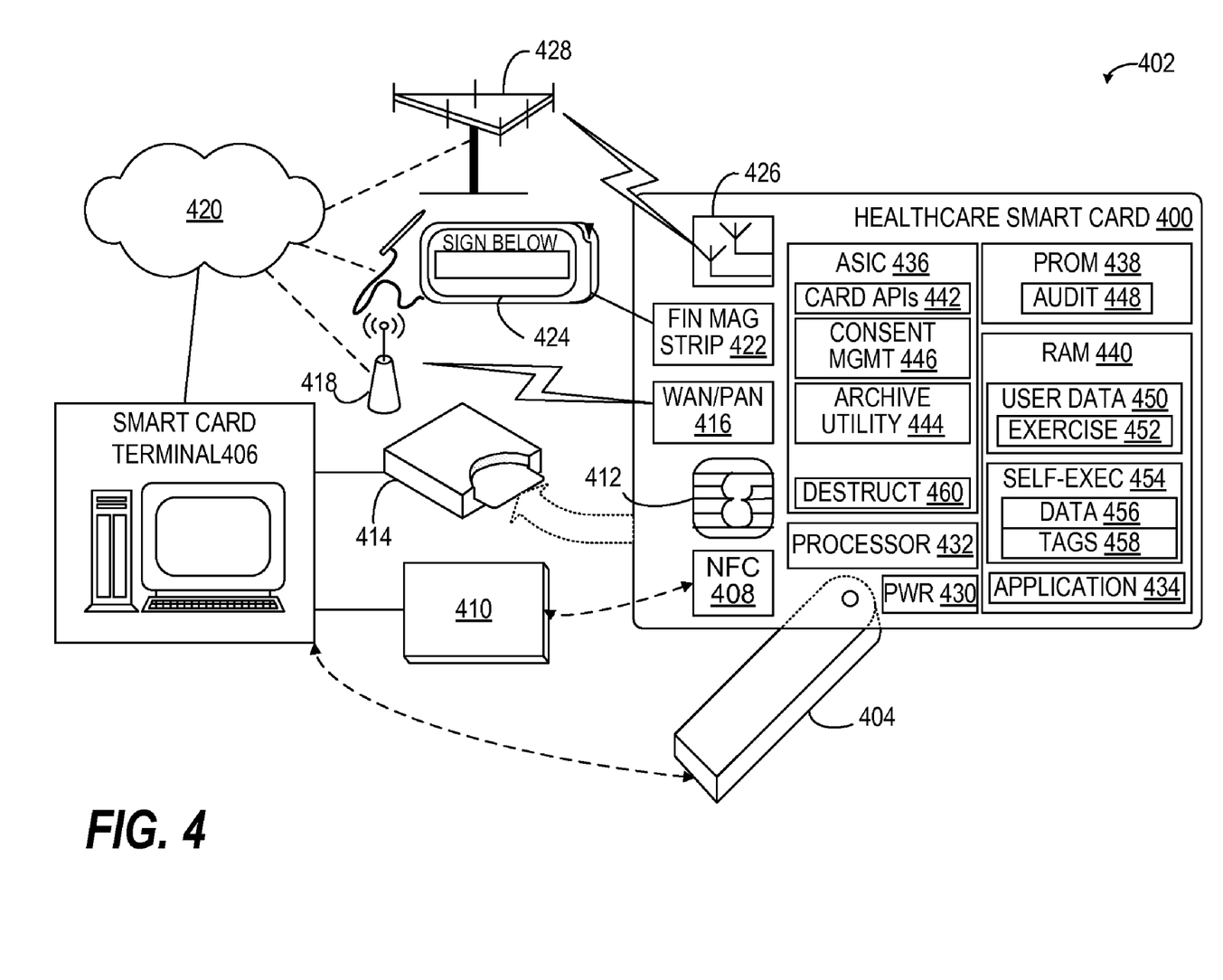
FIG. 4 illustrates a block diagram of an exemplary system for enhancing universality of a healthcare smart card incorporating multiple network interfaces.

In FIG. 4, an exemplary smart card 400 provides a plurality of network interfaces and functionality to serve the security, privacy and healthcare information needs of a plurality of stakeholders in a healthcare information system 402. For example, a computer interface, depicted as a pivoting USB male 404 plug allows direct access to a smart card terminal 406, such as a general purpose computer, expanding the population of possible devices that can utilize the smart card 400. A near field communication (NFC) antenna 408 can couple to an NFC accessory 410, providing advantages of reduced likelihood of connector wear and damage. Contacts 412 on the smart card 400 can interface with a card reader 414 to the smart card terminal 406. A wide area network (WAN)/personal area network (PAN) transceiver 416 can communicate with access point 418 to a network 420 connected to the smart card terminal 406. The smart card 400 can include a financial magnetic strip 422 for facilitating conventional credit card/debit transactions via a card swipe device 424. Alternatively or in addition, a radio frequency transceiver 426 of the smart card 400 can communicate with a radio access network 428 (e.g., cell phone, short message service, etc.).

The smart card 400 can include an autonomous power source 430 (e.g., battery), can be wirelessly induced with a charge such as via the received electromagnetic signal to charge a capacitive power source 430, or be directly power by the smart card terminal 406. This power activates a processor 432 that executes applications 434 contained in an Application Specific Integrated Circuit (ASIC) 436, a Programmable Read Only Memory (PROM) 438 or a Random Access Memory (RAM) 440. For example, the smart card 400 can have sufficient power to utilize volatile RAM 440. Alternatively, the RAM 430 can be nonvolatile.

To further enhance inoperability, the ASIC 436 is depicted as including Card Application Programming Interfaces 442 that can be accessed by the smart card terminal 406 to communicate with the smart card 400. A preconfigured or user implemented archive utility 444 can archive portions of data either upon receipt, later upon command or passage of time or upon shortage of storage capacity. The archive utility 444 can further take advantage of network connectivity to archive data as a backup for data integrity. Consent management utility 446 parses privileges such as access, edit and delete for data stored on the smart card 400 to enhance privacy, proprietary ownership, and integrity of data. Settings for consent management can be default, can be set during card issue, or be user specified after issue.

The PROM 438 can advantageously maintain an audit file 448 that tracks information suitable for referencing later for fraud mitigation, hacker protection, transaction confirmation, device troubleshooting, and malfunction mitigation. The RAM 440 can advantageously include user data structures 450, depicted as exercise data 452. RAM 440 can include self-executing data objects 454 containing data 456 with identifying tags 458 for querying and for privilege verification.

Figure 5:
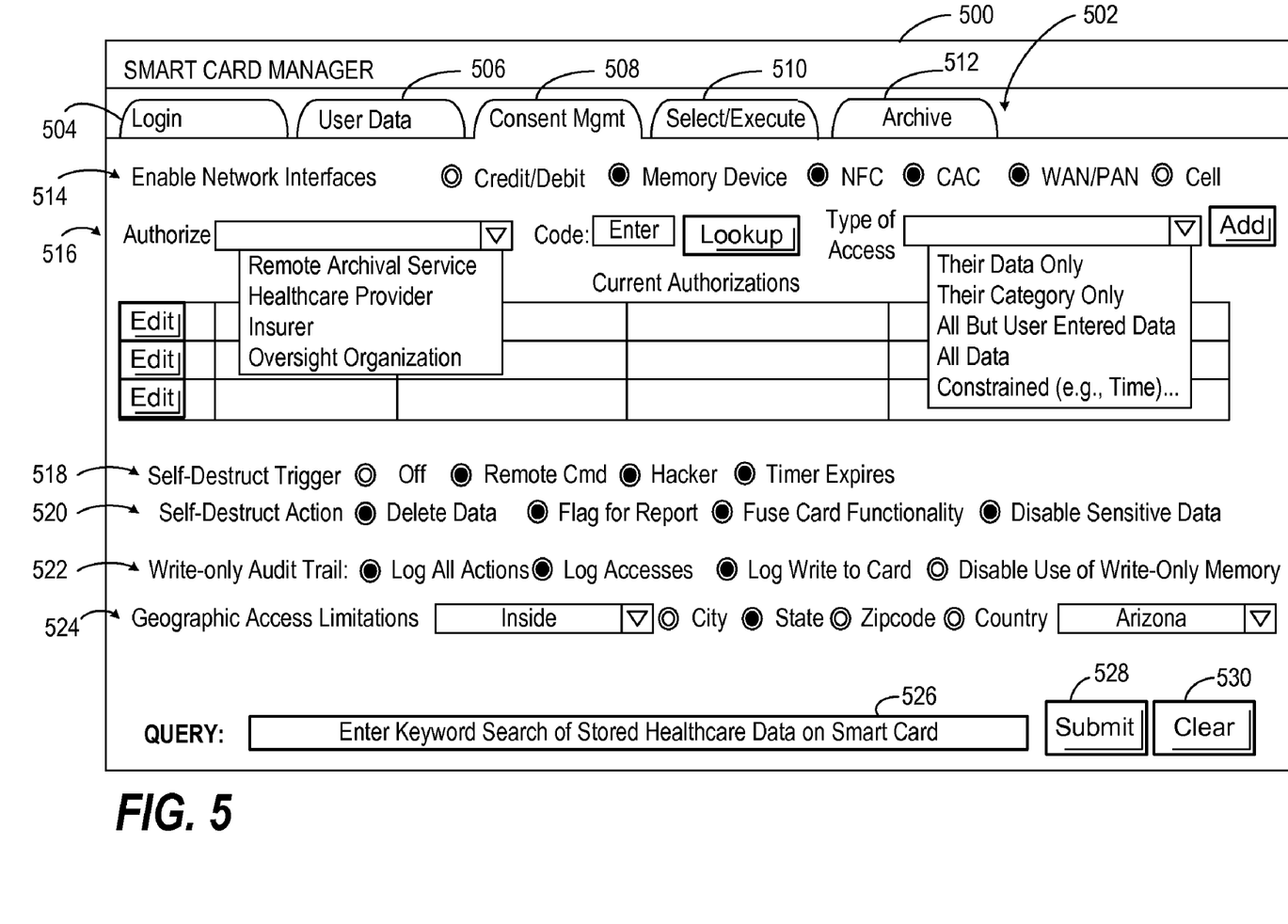
FIG. 5 illustrates a diagram of a graphical user interface for setting consent management for a healthcare smart card.

In FIG. 5, an illustrative graphical user interface 500 is rendering a smart card manager window 502, such as provided by a Smart Card API accessed on the smart card of FIG. 4. Multiple functions can be accessed, depicted as a User Login Tab 504, a User Data Tab 506, a Consent Management Tab 508, a Select/Execute Stored Data Object Tab 510, and an Archive Utility Tab 512. In the selected Consent Management Tab 508, Network Interface Enablement controls 514 have been selected to enable the smart card as a memory device, an NFC device, a common access card (CAC), WAN/PAN device while disabling use as a credit/debit card and a cell phone device. Privilege controls 516 can be set for each stakeholder (e.g., insurer, healthcare provider, archivist, etc.) for the privileges which the user has authority to change.

Self-destruct trigger controls 518 can be set for safeguarding the data, depicted as a remote command authorization, a hacker detection logic and timer expiration logic. When triggered, self-destruct action controls 520 can specify whether to delete data, flag for report during synchronization, fuse card functionality and/or to disable sensitive data only.

Write-only audit trail controls 522 can specify whether to log all actions, log accesses to card, log write actions to card, or disable use of the write-only memory.

Functionality, self-destruct or other features can be made responsive to geographic access limitation controls 524, depicted as setting a distance range according to city, state, zip code or country. This location could be determined by GPS signal, based upon network connection or other inputs.

The user can advantageously search for a particular data object stored on the card via a keyword search field 526 with a submit button 528 and a clear entry button 530.

Figure 6:
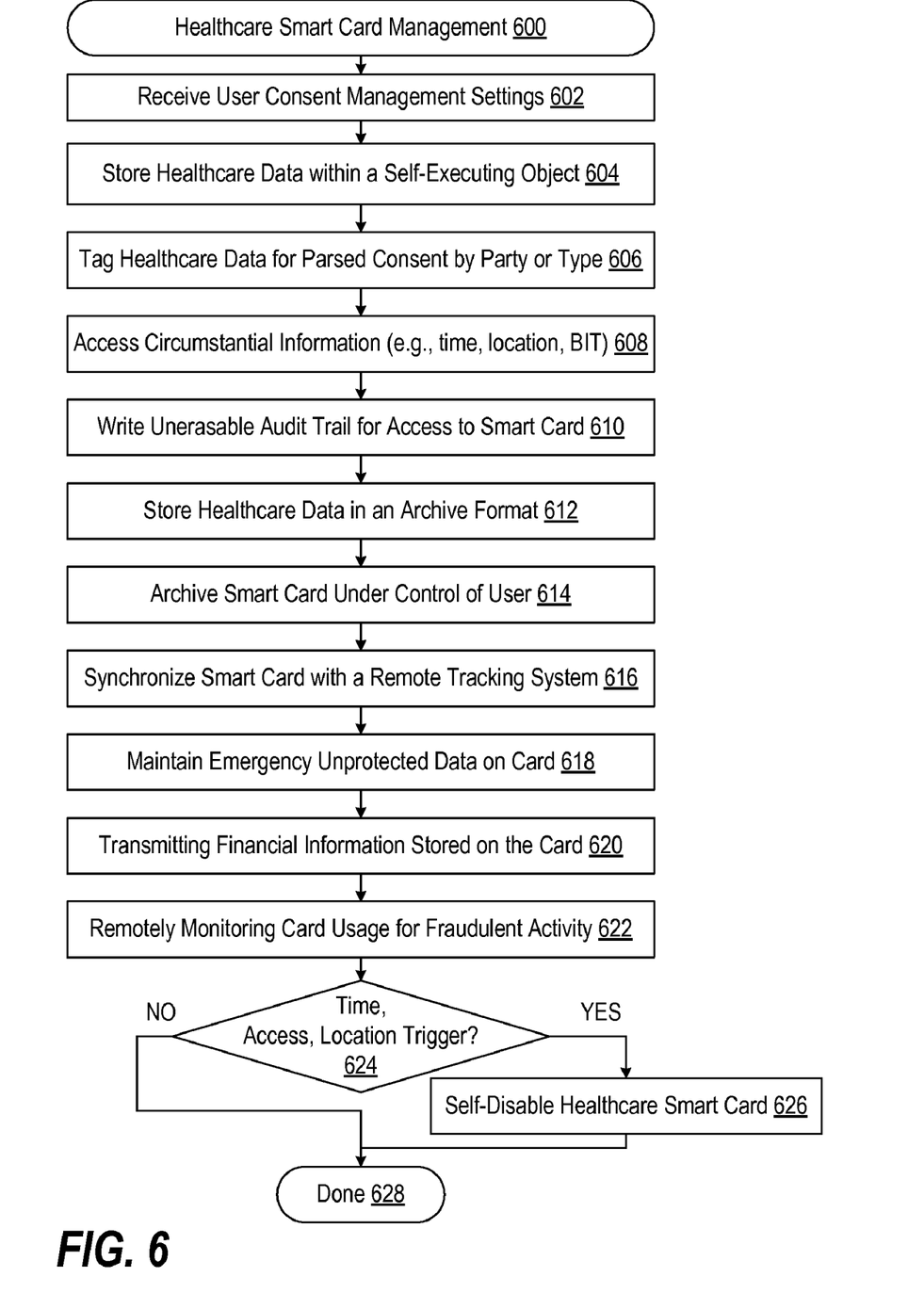
FIG. 6 illustrates a flow diagram of a methodology for parsing access of data, archiving of data, oversight of usage, and automatic destruction of a healthcare smart card.

FIG. 6 illustrates methodologies and/or flow diagrams in accordance with the claimed subject matter. For simplicity of explanation, the methodologies are depicted and described as a series of acts. It is to be understood and appreciated that the subject innovation is not limited by the acts illustrated and/or by the order of acts. For example acts can occur in various orders and/or concurrently, and with other acts not presented and described herein. Furthermore, not all illustrated acts may be required to implement the methodologies in accordance with the claimed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

A methodology 600 for healthcare smart card management enhances user privacy while recognizing diverse ownership and access interests in healthcare data by receiving user consent management settings in block 602. Healthcare data is stored within a self-executing object in block 604 in order to increase options for accessing the stored data. Healthcare data is tagged so that parsed consent can be implemented by party or type of party in block 606. In block 608, circumstantial information is accessed, such as a current date/time either locally maintained or accessed externally upon intermittent power up. Circumstantial information can further include location (e.g., global positioning system (GPS), network node identifier, etc.). Circumstantial information can further include current operating status for the smart card, to include detected malfunction or circuitry compromise.

In block 610, a write-only, unerasable audit trail is recorded on the smart card for events such as access to the data and the circumstantial information. This audit trail can be useful in thwarting fraudulent use, to overcome malfunctions, to trigger reporting or self-protection measures, etc.

In block 612, healthcare data is stored in archive format. Such archiving can increase the resolution of healthcare documentation (e.g., scanned documents) to preserve memory capacity. Archiving format can facilitate expeditious transmission to remote archiving. The archiving format can overlay an overall encryption protection over separately protected discrete data elements. Some of these archiving functions can be controlled by a user as depicted in block 614 to enhance actual or perceived privacy and data integrity.

In block 616, the smart card is synchronized with a remote tracking system. For example, a card issuer could receive a subset of the healthcare data that merely shows authentication access so that improper access is detected. This card issuer could facilitate transfer of authentication/access keys to successors in interest, such as a new insurer or healthcare provider. Such synchronization can take advantage of periodic communication with a network-enabled smart card terminal.

In block 618, synchronization or direct smart card terminal interaction can be used to add user and emergency unprotected data on the smart card. The user or trusted third party can augment the functionality of the healthcare smart card by storing data such as a testamentary will, living will, durable power of attorney for healthcare decisions, emergency locator information, citizenship, medical conditions for first responders (e.g., blood type, allergies, chronic diseases, age, types/locations of medical implants that limit diagnostic imaging, etc.), dietary journal or dietary restrictions, prescribed medications, exercise regimen, etc.

Functionality of the healthcare smart card can be further enhanced in block 622 by providing the necessary network interfaces and financial transaction authorization codes in order to facilitate a financial transaction with the same card.

For either financial or healthcare transactions, portions of the data are monitored remotely for fraud in block 622. For example, with a more universally acceptable medium for facilitating healthcare information exchange, an independent oversight authority (e.g., state or federal regulatory agency) can detect contemporaneous usage of the card in different locations or with unmatched user identification, etc.

In block 624, the circumstantial information, audit trail, etc, can trigger a preset condition (e.g., time since synchronization, expiration of a time limit, use in a geographic location outside of permissible boundary, malfunction, repeated attempts to hack the identity or data of the smart card). If so determined, then the smart card can self-disable at least a portion of itself (e.g., erasure, circuitry fusing, etc.) in block 626 and then the methodology is done in block 628.

Figure 7:
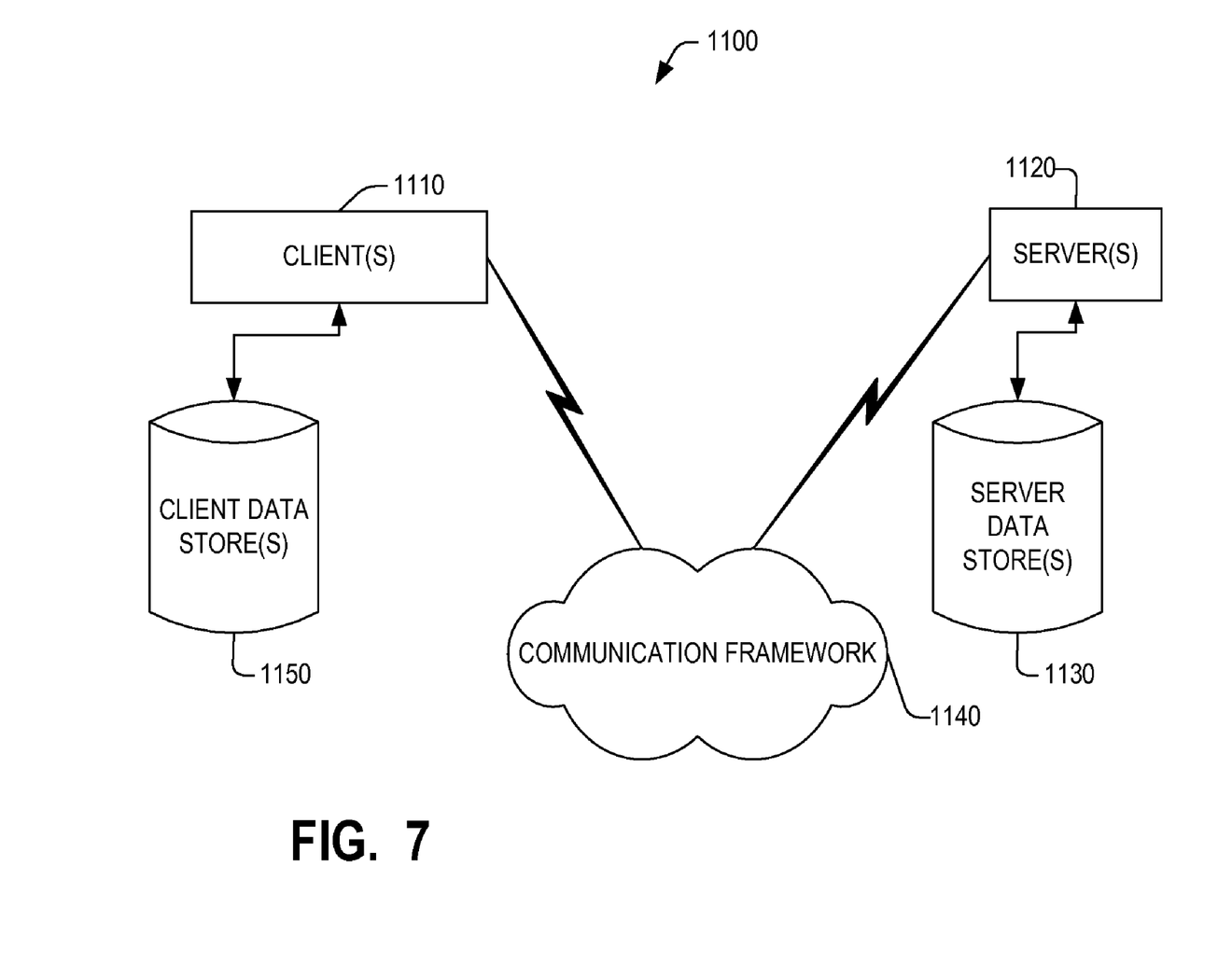
FIG. 7 illustrates an exemplary networking environment, wherein the novel aspects of the claimed subject matter can be employed.
Figure 8:
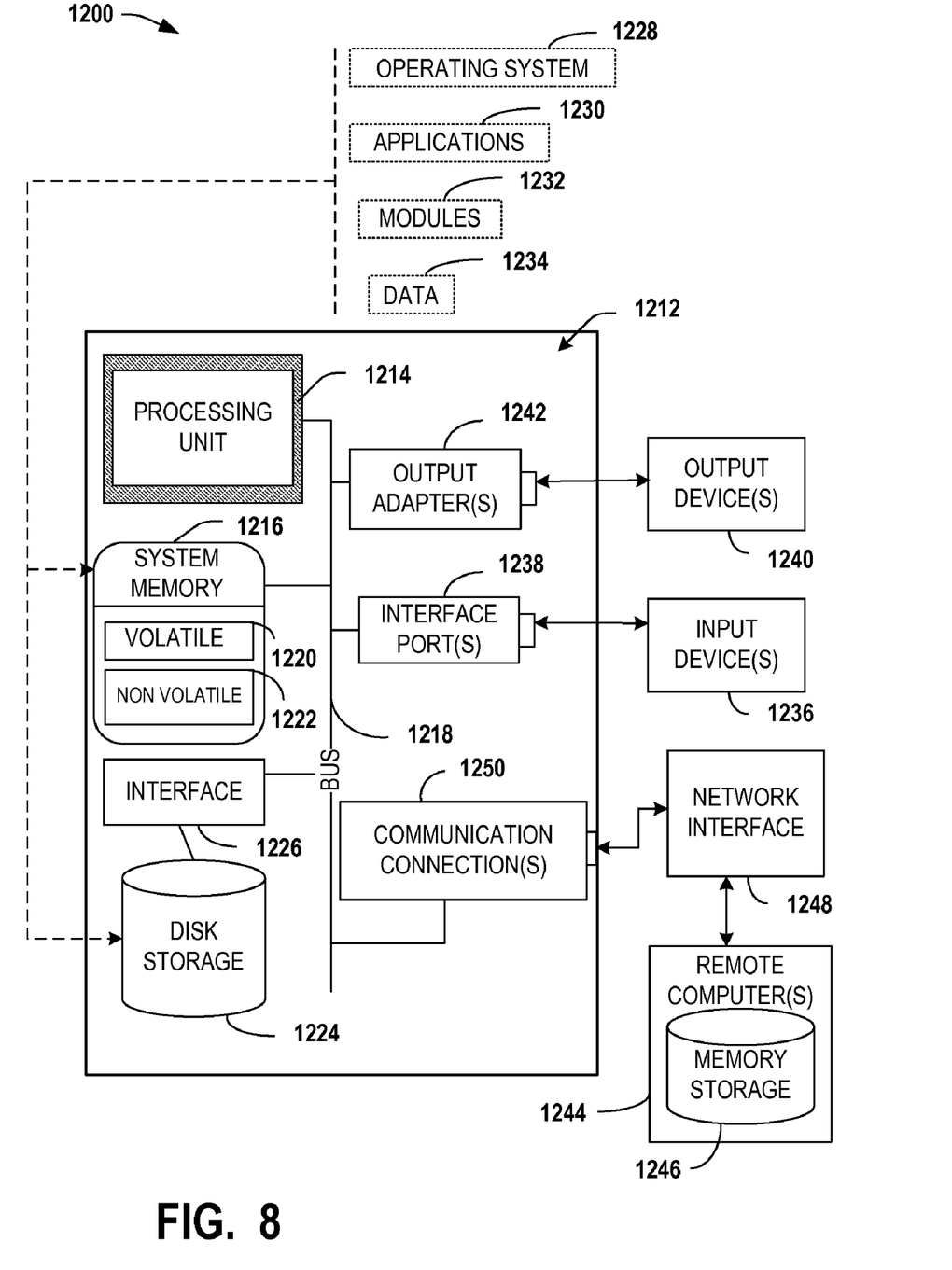
FIG. 8 illustrates an exemplary operating environment that can be employed in accordance with the claimed subject matter.

In order to provide additional context for implementing various aspects of the claimed subject matter, FIGS. 7-8 and the following discussion is intended to provide a brief, general description of a suitable computing environment in which the various aspects of the subject innovation may be implemented. For example, a counselor component that facilitates automatically generating questions to ask a doctor during an appointment, as described in the previous figures, can be implemented in such suitable computing environment. While the claimed subject matter has been described above in the general context of computer-executable instructions of a computer program that runs on a local computer and/or remote computer, those skilled in the art will recognize that the subject innovation also may be implemented in combination with other program modules. Generally, program modules include routines, programs, components, data structures, etc., that perform particular tasks and/or implement particular abstract data types.

Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the claimed subject matter may also be practiced in distributed computing environments where certain tasks are performed by remote processing devices that are linked through a communications network. However, some, if not all, aspects of the subject innovation may be practiced on stand-alone computers. In a distributed computing environment, program modules may be located in local and/or remote memory storage devices.

FIG. 7 is a schematic block diagram of a sample-computing environment 1100 with which the claimed subject matter can interact. The system 1100 includes one or more client(s) 1110. The client(s) 1110 can be hardware and/or software (e.g., threads, processes, computing devices). The system 1100 also includes one or more server(s) 1120. The server(s) 1120 can be hardware and/or software (e.g., threads, processes, computing devices). The servers 1120 can house threads to perform transformations by employing the subject innovation, for example.

One possible communication between a client 1110 and a server 1120 can be in the form of a data packet adapted to be transmitted between two or more computer processes. The system 1100 includes a communication framework 1140 that can be employed to facilitate communications between the client(s) 1110 and the server(s) 1120. The client(s) 1110 are operably connected to one or more client data store(s) 1150 that can be employed to store information local to the client(s) 1110. Similarly, the server(s) 1120 are operably connected to one or more server data store(s) 1130 that can be employed to store information local to the servers 1120.

With reference to FIG. 8, an exemplary environment 1200 for implementing various aspects of the claimed subject matter includes a computer 1212. The computer 1212 includes a processing unit 1214, a system memory 1216, and a system bus 1218. The system bus 1218 couples system components including, but not limited to, the system memory 1216 to the processing unit 1214. The processing unit 1214 can be any of various available processors. Dual microprocessors and other multiprocessor architectures also can be employed as the processing unit 1214.

The system bus 1218 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCM-CIA), Firewire (IEEE 1394), and Small Computer Systems Interface (SCSI).

The system memory 1216 includes volatile memory 1220 and nonvolatile memory 1222. The basic input/output system (BIOS), containing the basic routines to transfer information between elements within the computer 1212, such as during start-up, is stored in nonvolatile memory 1222. By way of illustration, and not limitation, nonvolatile memory 1222 can include read only memory (ROM), programmable ROM (PROM), electrically programmable ROM (EPROM), electrically erasable programmable ROM (EEPROM), or flash memory. Volatile memory 1220 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1212 also includes removable/non-removable, volatile/non-volatile computer storage media. FIG. 8 illustrates, for example, disk storage 1224. Disk storage 1224 includes, but is not limited to, devices like a magnetic disk drive, floppy disk drive, tape drive, Jaz drive, Zip drive, LS-100 drive, flash memory card, or memory stick. In addition, disk storage 1224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1224 to the system bus 1218, a removable or non-removable interface is typically used such as interface 1226.

It is to be appreciated that FIG. 7 describes software that acts as an intermediary between users and the basic computer resources described in the suitable operating environment 1200. Such software includes an operating system 1228. Operating system 1228, which can be stored on disk storage 1224, acts to control and allocate resources of the computer system 1212. System applications 1230 take advantage of the management of resources by operating system 1228 through program modules 1232 and program data 1234 stored either in system memory 1216 or on disk storage 1224. It is to be appreciated that the claimed subject matter can be implemented with various operating systems or combinations of operating systems.

A user enters commands or information into the computer 1212 through input device(s) 1236. Input devices 1236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1214 through the system bus 1218 via interface port(s) 1238. Interface port(s) 1238 include, for example, a serial port, a parallel port, a game port, and a universal serial bus (USB). Output device(s) 1240 use some of the same type of ports as input device(s) 1236. Thus, for example, a USB port may be used to provide input to computer 1212 and to output information from computer 1212 to an output device 1240. Output adapter 1242 is provided to illustrate that there are some output devices 1240 like monitors, speakers, and printers, among other output devices 1240, which require special adapters. The output adapters 1242 include, by way of illustration and not limitation, video and sound cards that provide a means of connection between the output device 1240 and the system bus 1218. It should be noted that other devices and/or systems of devices provide both input and output capabilities such as remote computer(s) 1244.

Computer 1212 can operate in a networked environment using logical connections to one or more remote computers, such as remote computer(s) 1244. The remote computer(s) 1244 can be a personal computer, a server, a router, a network PC, a workstation, a microprocessor based appliance, a peer device or other common network node and the like, and typically includes many or all of the elements described relative to computer 1212. For purposes of brevity, only a memory storage device 1246 is illustrated with remote computer(s) 1244. Remote computer(s) 1244 is logically connected to computer 1212 through a network interface 1248 and then physically connected via communication connection 1250. Network interface 1248 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1250 refers to the hardware/software employed to connect the network interface 1248 to the bus 1218. While communication connection 1250 is shown for illustrative clarity inside computer 1212, it can also be external to computer 1212. The hardware/software necessary for connection to the network interface 1248 includes, for exemplary purposes only, internal and external technologies such as, modems including regular telephone grade modems, cable modems and DSL modems, ISDN adapters, and Ethernet cards.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

There are multiple ways of implementing the present innovation, e.g., an appropriate API, tool kit, driver code, operating system, control, standalone or downloadable software object, etc. which enables applications and services to use the advertising techniques of the invention. The claimed subject matter contemplates the use from the standpoint of an API (or other software object), as well as from a software or hardware object that operates according to the advertising techniques in accordance with the invention. Thus, various implementations of the innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method of facilitating healthcare information exchange via a smart card, comprising:
    writing a self-executing object in the memory of the healthcare smart card, wherein the self-executing object increases options for legacy systems to access data that the legacy systems are not configured to access;
    authenticating a first party accessing a healthcare smart card, wherein the healthcare smartcard is a physical device having a patient's medical record stored in the memory of the healthcare smart card;
    storing a first data object within the self-executing object in the memory of the healthcare smart card having access limited to the first party via a user interface functionality provided by the self-executing object;
    authenticating a second party accessing the healthcare smart card; and
    storing a limited object in the memory of the healthcare smart card having access limited to the second party; and
    receiving the self-executing object as a print to device function by utilizing the smart card as a flash memory device for the legacy systems that are unable to interact with the functionality of the smart card.

2. The method of claim 1, wherein the first data object is stored in an access form and the second data object is stored in an archived format.

3. The method of claim 1, wherein the first party comprises a user assigned to the healthcare smart card.

4. The method of claim 1, wherein the second party comprises a selected one of a group consisting of a remote archival service, an access oversight entity, and a healthcare provider.

5. The method of claim 1, further comprising a financial network interface for authorizing a healthcare payment transaction.

6. The method of claim 1, further comprising interfacing to a plurality of network interfaces comprising a near field communication transceiver, a wireless access network base node, and a card reader.

7. The method of claim 1, further comprising:
    tagging the first and second data objects with a data category to facilitate query and privilege verification; and
    setting consent management for the healthcare smart card to enable access to a selected data category tag to a third party assigned to the selected data category.

8. The method of claim 1, further comprising monitoring disabling access to one of the data objects in response to detecting a data denial condition.

9. The method of claim 8, further comprising a selected condition from a group consisting of detecting an expiration of a timer; access outside of a specified geographic area; repeated attempts to access without recognized authentication, and abnormal operation of the healthcare smart card.

10. The method of claim 1, further comprising writing a permanent audit record on the healthcare smart card.

11. The method of claim 10, further comprising writing an audit record to log a complete set of access attempts, read transactions, write transactions, financial data transactions, and consent management setting changes.

12. The method of claim 1, wherein the executable object written to the healthcare smart card is computer platform-independent.

13. The method of claim 1, further setting consent management settings for the healthcare smart card input on a user graphical interface.

14. The method of claim 1, further comprising synchronizing a remote data storage with a portion of content of the healthcare smart card in response to network enabled device access to the healthcare smart card.

15. The method of claim 1, further comprising allowing universal access to time critical healthcare data stored on the healthcare smart card.

16. The method of claim 15, further comprising data selected from a group consisting of citizenship, critical healthcare conditions of the user for first responders, and emergency contact information.

* * * * *